(12) United States Patent
Hareyama

(10) Patent No.: US 6,511,476 B2
(45) Date of Patent: Jan. 28, 2003

(54) ELECTROSURGICAL APPARATUS WITH STABLE COAGULATION

(75) Inventor: Norihiko Hareyama, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/992,457

(22) Filed: Nov. 14, 2001

(65) Prior Publication Data

US 2002/0032439 A1 Mar. 14, 2002

Related U.S. Application Data

(63) Continuation of application No. 09/449,129, filed on Nov. 24, 1999.

(30) Foreign Application Priority Data

Nov. 27, 1998 (JP) .............................. 10-337034
Jan. 14, 1999 (JP) .......................... 11-007523

(51) Int. Cl.[7] .............................. A61B 18/18
(52) U.S. Cl. ...................... 606/34; 606/38; 606/41; 606/42; 606/50
(58) Field of Search .............................. 606/32, 34, 38, 606/40, 41, 42, 46, 48, 50; 607/98, 101, 102, 122

(56) References Cited

U.S. PATENT DOCUMENTS

| | | |
|---|---|---|
| 4,474,179 A | 10/1984 | Koch |
| 5,437,664 A | 8/1995 | Cohen et al. |
| 5,540,684 A | 7/1996 | Hassler, Jr. |
| 5,558,671 A | 9/1996 | Yates |
| 5,733,281 A | 3/1998 | Nardella |
| 5,817,093 A | 10/1998 | Williamson, IV et al. |
| 5,836,943 A | 11/1998 | Miller, III |
| 5,931,836 A | 8/1999 | Hatta et al. |
| 5,954,717 A | 9/1999 | Behl et al. |
| 6,033,399 A | 3/2000 | Gines |
| 6,132,429 A | 10/2000 | Baker |

FOREIGN PATENT DOCUMENTS

JP     8-196543     8/1996

*Primary Examiner*—Linda C. M. Dvorak
*Assistant Examiner*—David M. Ruddy
(74) *Attorney, Agent, or Firm*—Scully, Scott, Murphy & Presser

(57) ABSTRACT

An electrosurgical apparatus supplies high-frequency power from a high-frequency power supply unit to an instrument placed in association with an organic tissue to dissect or coagulate the organic tissue. An impedance calculating section calculates the impedance value of the organic tissue. A rate-of-impedance-change calculating section calculates the rate of impedance change of the organic tissue based on the impedance value calculated by the impedance calculating section. A control section controls the high-frequency output of the high-frequency power supply unit based on a predetermined condition provided by combining the impedance value calculated by the impedance calculating section with the rate of impedance change calculated by the rate-of-impedance-change calculating section.

5 Claims, 14 Drawing Sheets

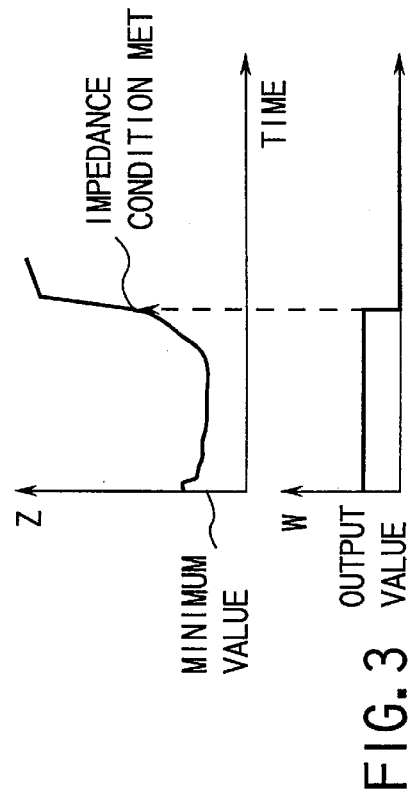
FIG. 1
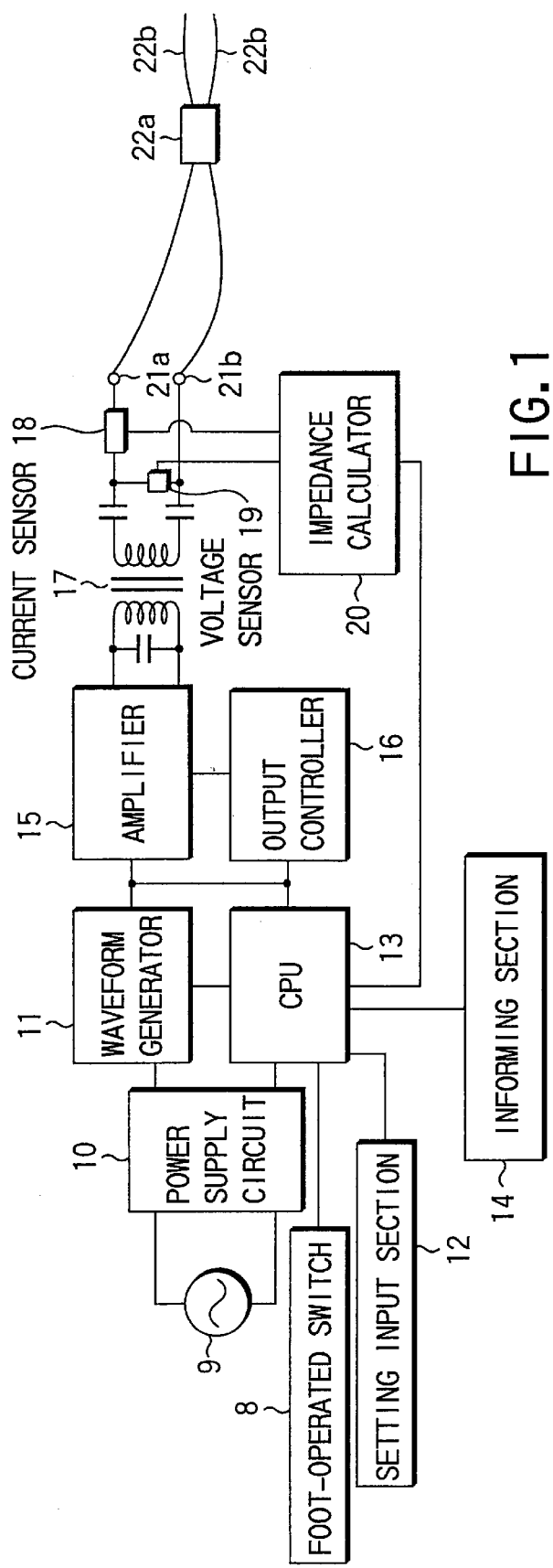
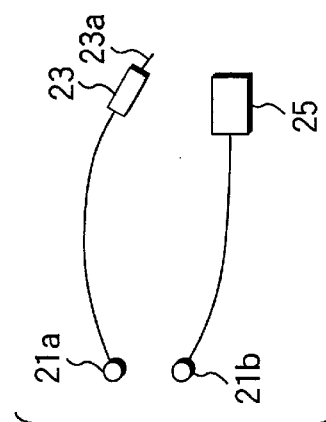
FIG. 2
FIG. 3

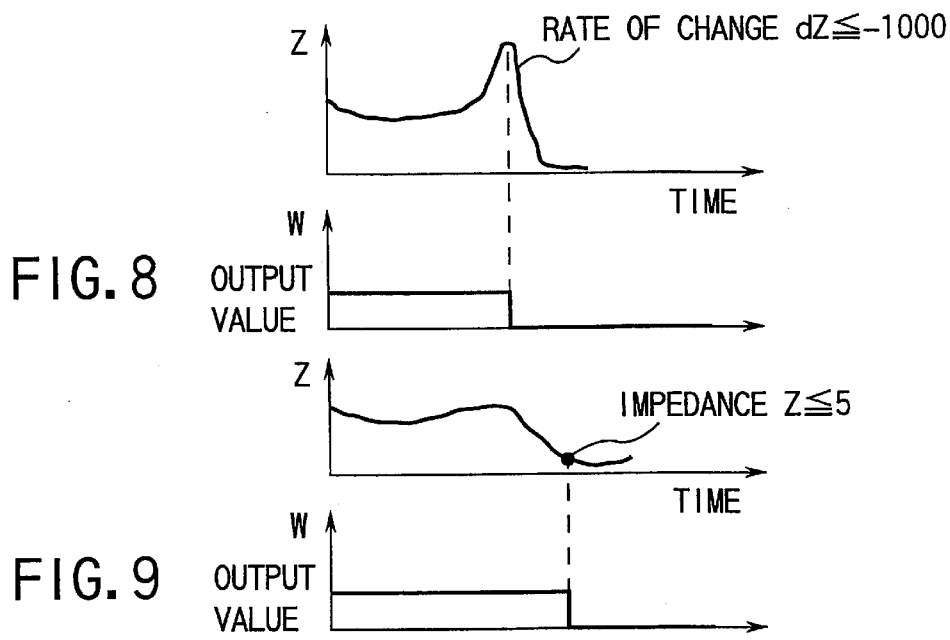
FIG. 8
FIG. 9
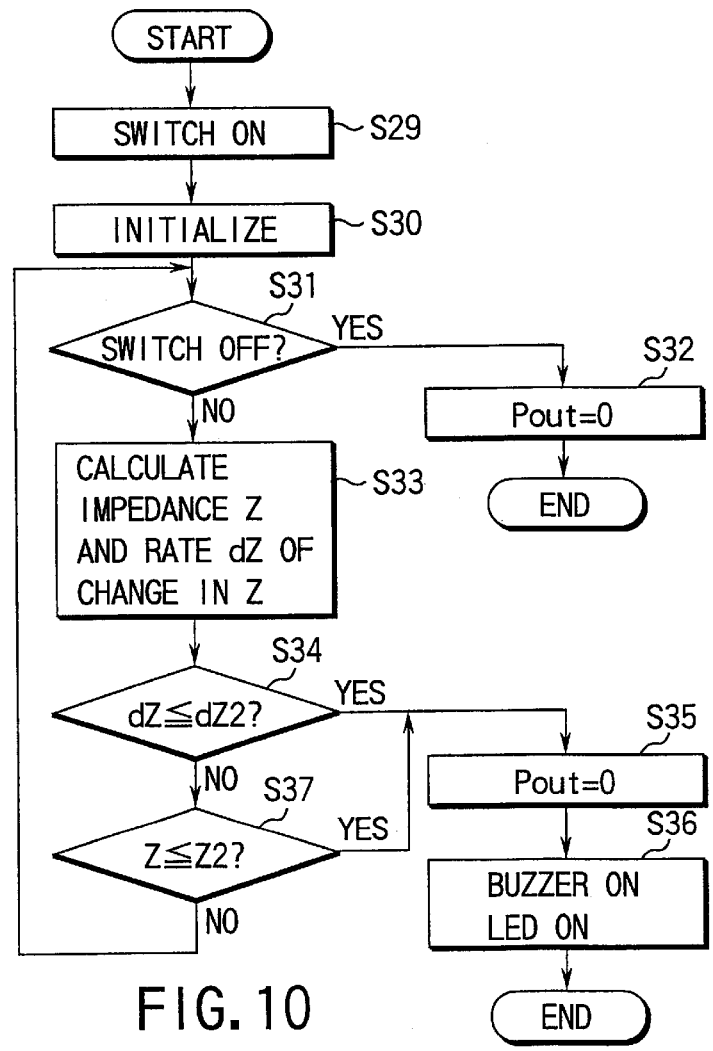
FIG. 10

ELECTROSURGICAL APPARATUS WITH STABLE COAGULATION

CROSS REFERENCE TO RELATED APPLICATIONS

This application is a continuation of U.S. application Ser. No. 09/449,129, filed on Nov. 24, 1999.

BACKGROUND OF THE INVENTION

The present invention relates to an electro-surgical apparatus.

There are electrosurgical apparatuses which coagulate or dissect organic tissues using high-frequency power. Such an electrosurgical apparatus generates high-frequency power inside its main body and supplies the high-frequency power to a monopolar instrument or bipolar instrument, connected to the main body, for treatment of organic tissues.

Jpn. Pat. Appln. KOKAI Publication No. 8-196543 discloses an impedance monitoring apparatus which monitors the impedance of an organic tissue while this tissue is being treated with high-frequency power. More specifically, this apparatus measures the minimum impedance and uses a function of this minimum impedance to determine the impedance of the point of time when tissue coagulation is completed.

As the electrosurgical apparatus described in the aforementioned Jpn. Pat. Appln. KOKAI Publication No. 8-196543 detects the end of tissue coagulation based only on the function of the minimum impedance, the detection result considerably varies depending on the types of tissues or the clamping state of forceps, which may result in overburning. Apparently, this apparatus cannot guarantee a stable coagulation performance.

There is another method which detects the end of tissue coagulation using the rate of change in impedance, but which has a drawback similar to that of the above method of detecting the end of tissue coagulation using the impedance.

The prior art including the one disclosed in the mentioned Jpn. Pat. Appln. KOKAI Publication No. 8-196543 employs fixed conditions for detecting the end of tissue coagulation and thus cannot arbitrarily change the coagulation level.

Accordingly, it is a primary object of the present invention to provide an electrosurgical apparatus capable of surely stopping the output at the end of coagulation to avoid overburning.

It is a secondary object of this invention to provide an electrosurgical apparatus which can change the coagulation level according to a user's selection by changing a condition for detecting the end of coagulation.

BRIEF SUMMARY OF THE INVENTION

To achieve the first object, according to the first aspect of this invention, there is provided an electrosurgical apparatus for supplying high-frequency power from a high-frequency power supply unit to an instrument placed in association with an organic tissue to dissect or coagulate the organic tissue, which said electrosurgical apparatus comprises:

an impedance calculating section for calculating an impedance value of the organic tissue;

a rate-of-impedance-change calculating section for calculating a rate of impedance change of the organic tissue based on the impedance value calculated by the impedance calculating section; and a control section for controlling a high-frequency output of the high-frequency power supply unit based on a predetermined condition provided by an evaluation of both the impedance value calculated by the impedance calculating section and the rate of impedance change calculated by the rate-of-impedance-change calculating section.

To achieve the first object, according to the second aspect of this invention, there is provided a control apparatus, connected to an electrosurgical apparatus having an instrument for performing a predetermined treatment on an organic tissue and a high-frequency power supply unit for supplying high-frequency power for treating the organic tissue to the instrument, for controlling the high-frequency power output from the high-frequency power supply unit, which control apparatus comprises:

an impedance calculating section for calculating an impedance value of the organic tissue;

a rate-of-impedance-change calculating section for calculating a rate of impedance change of the organic tissue based on the impedance value calculated by the impedance calculating section; and a control section for controlling a high-frequency output of the high-frequency power supply unit based on a predetermined condition provided by combining the impedance value calculated by the impedance calculating section with the rate of impedance change calculated by the rate-of-impedance-change calculating section.

To achieve the second object, according to the third aspect of this invention, there is provided an electrosurgical apparatus for supplying high-frequency power from a high-frequency power supply unit to an instrument placed in association with an organic tissue to coagulate or dissect the organic tissue, which apparatus comprises:

a setting section for setting a coagulation level comprising at least one variable representing an end of coagulation in a variable manner prior to a coagulation operation;

a detection section for detecting a coagulation state of the organic tissue in a coagulation operation; and a control section for controlling a high-frequency output of the high-frequency power supply unit based on the coagulation level set by the setting section and the coagulation state detected by the detection section.

To achieve the second object, according to the fourth aspect of this invention, there is provided a control apparatus, connected to an electrosurgical apparatus having an instrument for performing a predetermined treatment on an organic tissue and a high-frequency power supply unit for supplying high-frequency power for treating the organic tissue to the instrument, for controlling the high-frequency power output from the high-frequency power supply unit, which control apparatus comprises:

a setting section for setting a coagulation level of a tissue in a variable manner;

a detection section for detecting a coagulation state of the organic tissue in a coagulation operation; and a control section for controlling a high-frequency output of the high-frequency power supply unit based on the coagulation level set by the setting section and the coagulation state detected by the detection section.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a diagram illustrating the internal structure of an electrosurgical apparatus according to embodiments of this invention;

FIG. 2 is a diagram showing a monopolar instrument;

FIG. 3 is a diagram for explaining the operations of first to third embodiments of this invention;

FIG. 8 is a diagram (part 1) for explaining the operation of a fourth embodiment of this invention;

FIG. 9 is a diagram (part 2) for explaining the operation of the fourth embodiment of this invention;

FIG. 10 is a flowchart illustrating the operation of the fourth embodiment of this invention;

DETAILED DESCRIPTION OF THE INVENTION

Figure 5:
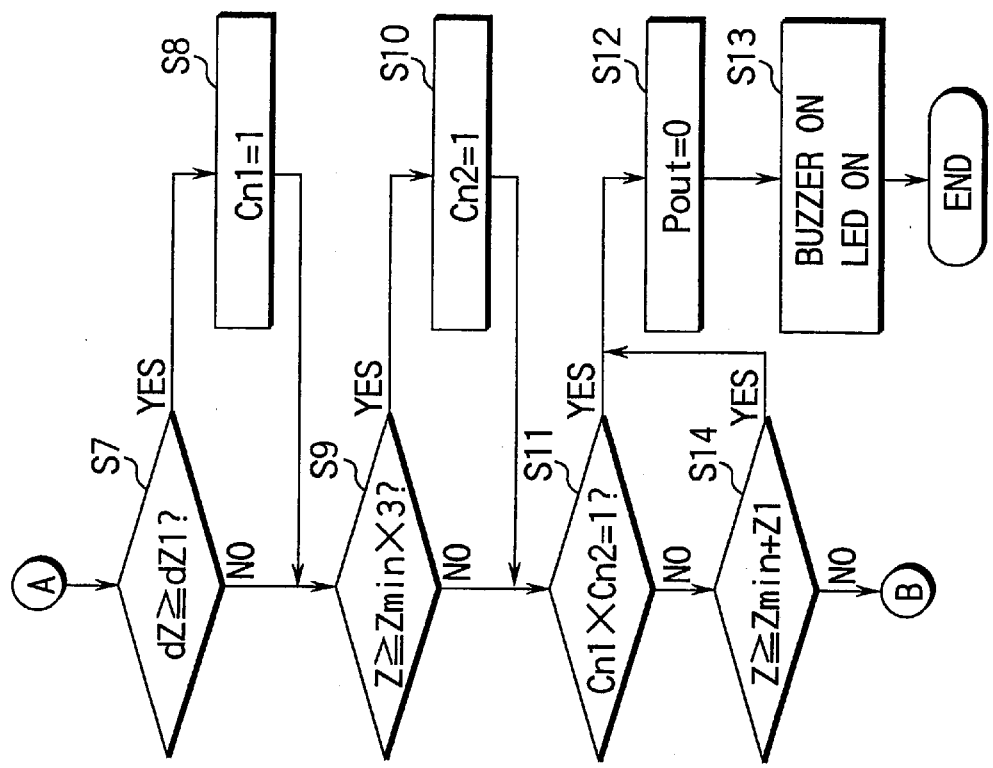
FIG. 5 is a flowchart showing steps between A and B in FIG. 4.

Preferred embodiments of the present invention will now be described in detail with reference to the accompanying drawings.

FIG. 1 is a diagram illustrating the internal structure of an electrosurgical apparatus according to embodiments of this invention. A commercially available power supply 9 is connected to a power supply circuit 10 which generates desired supply power. Connected to this power supply circuit 10 are a waveform generator 11 which generates a waveform corresponding to the output mode according to a procedure and a CPU 13 for implementing general control of this electrosurgical apparatus. Connected to the waveform generator 11 and the CPU 13 are an amplifier 15 for amplifying a minute-level signal from the waveform generator 11 and an output controller 16 for controlling the output of the amplifier 15 based on a control signal from the CPU 13.

An output transformer 17 has its primary side connected to the amplifier 15 and its secondary side connected to terminals 21a and 21b via a current sensor 18 and a voltage sensor 19. A bipolar instrument 22a and bipolar electrode 22b are connected via active lines to the terminals 21a and 21b.

Although the bipolar instrument is illustrated as an instrument in FIG. 1, a monopolar instrument 23 with a monopolar electrode 23a may be used instead as shown in FIG. 2. In this case, a feedback electrode 25 is connected to the terminal 21b via a feedback line.

Connected to the current sensor 18 and voltage sensor 19 is an impedance calculator 20 which computes an impedance based on a current and a voltage respectively detected by those sensors 18 and 19. The CPU 13 is further connected to a foot-operated switch 8, a setting input section 12 and an informing section 14.

First Embodiment

A first embodiment of this invention will now be discussed with reference to the accompanying drawings. The first embodiment is characterized in that the CPU 13 and output controller 16 control the amplifier 15 to stop the output (automatic stop function) when a combination of the impedance of a tissue computed by the impedance calculator 20 and the rate of impedance change acquired based on this impedance meets a predetermined impedance condition.

FIG. 3 shows the relationship between the characteristic of an impedance (Z) and the output of the power supply circuit 10 and shows that the output of the amplifier 15 is stopped when the impedance condition is met.

Figure 4:
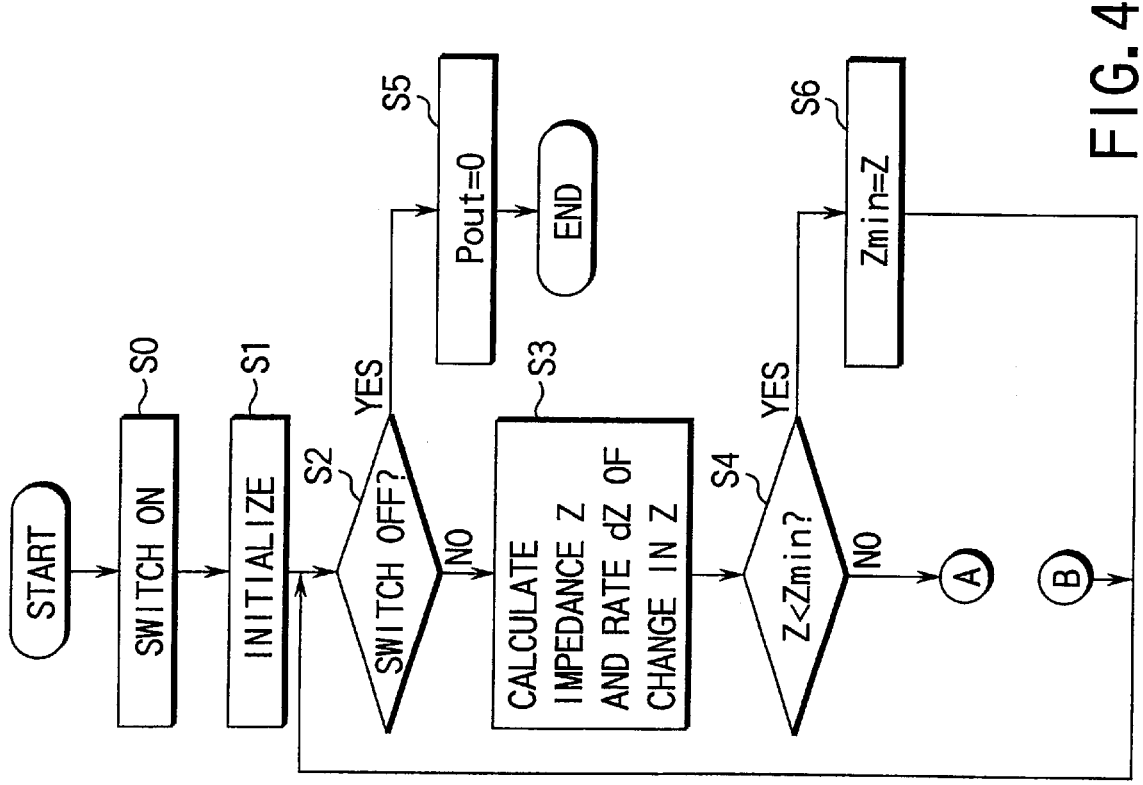
FIG. 4 is a flowchart illustrating the operation of the first embodiment of this invention.

The operation of the first embodiment will now be explained referring to a flowchart in FIG. 4.

As the foot-operated switch 8 for starting the power output from the electrosurgical apparatus is switched ON (step S0), initialization is executed (step S1). In this initialization, the output power P1=40 W input by an operator via the setting input section 12 is set to a variable Pout associated with the output power and 10 K Ω is set to a variable Zmin associated with the minimum impedance value. It is assumed that an initial impedance Z1 has been set to 500Ω, an initial rate of impedance change dZ1 has been set to +300 Ω/sec and a decision variable Cn1=0 and a decision variable Cn2=0 have been set.

Then, it is determined if the foot-operated switch 8 has been switched OFF (step S2). When the foot-operated switch 8 has been switched OFF, "0" is set to the output power Pout (step S5) after which this flow will be terminated. When the foot-operated switch 8 has not been switched OFF, an impedance Z and a rate of impedance change dZ are calculated (step S3). Next, it is determined if the calculated impedance Z is smaller than the minimum impedance value Zmin (step S4). When the decision is "YES," the calculated impedance Z is substituted into the minimum impedance value Zmin (step S6) and the flow then returns to step S2.

When the decision in step S4 is "NO," on the other hand, the flow proceeds to step S7 in FIG. 5 to determine if the calculated rate of impedance change dZ is equal to or greater than dZ1 (+300 Ω/sec in this example). When the decision is "YES," "1" is substituted into the decision variable Cn1 (step S8) and the flow then proceeds to step S9. When the decision in step S7 is "NO," the flow immediately proceeds to step S9.

In step S9, it is determined if the impedance Z is equal to or greater than the minimum impedance value Zmin multiplied by 3. When the decision is "YES," "1" is substituted into the decision variable Cn2 (step S10) and the flow then proceeds to step S11. When the decision in step S9 is "NO" the flow immediately proceeds to step S11.

In step S11, it is determined if the product of Cn1 and Cn2 is equal to "1." When the decision is "YES," "0" is substituted into the output power Pout (step S12), and the informing section 14 outputs a sound (buzzer ON) from a speaker or turns on an LED (step S13) to inform the operator. This flow is then terminated.

When the decision in step S11 is "NO," it is determined if the impedance Z is equal to or greater than the sum of the minimum impedance value Zmin and the initial impedance value Zini (step S14). When the decision is "YES," the processes starting at the aforementioned step S12 are executed. When the decision in step S14 is "NO," the flow returns to step S2 in FIG. 4.

The above-described first embodiment is summarized as follows.
(1) The output is started and the impedance value Z is measured.
(2) The minimum impedance value Zmin is acquired.
(3) The output is stopped when the impedance value Z satisfies either one of the following conditions (a) and (b).
 (a) The rate of impedance change dZ has become equal to or greater than +300 Ω/sec at least once and the impedance value Z has become equal to or greater than the minimum impedance value Zmin multiplied by 3.
 (b) The impedance value Z has become equal to or greater than the sum of the minimum impedance value Zmin and 500Ω.
(4) After the output is stopped in (3) above, the operator is informed through a buzzer sound or lit LED.

According to the above-described first embodiment, when the impedance rapidly rises which it indicates the end of coagulation, the condition (a) can surely stop the output. Even if the impedance rises too slowly to satisfy the condition (a), the output can be stopped using the condition (b). It is therefore possible to reliably stop the output at the end of coagulation where there is no overburning.

Second Embodiment

Figure 6:
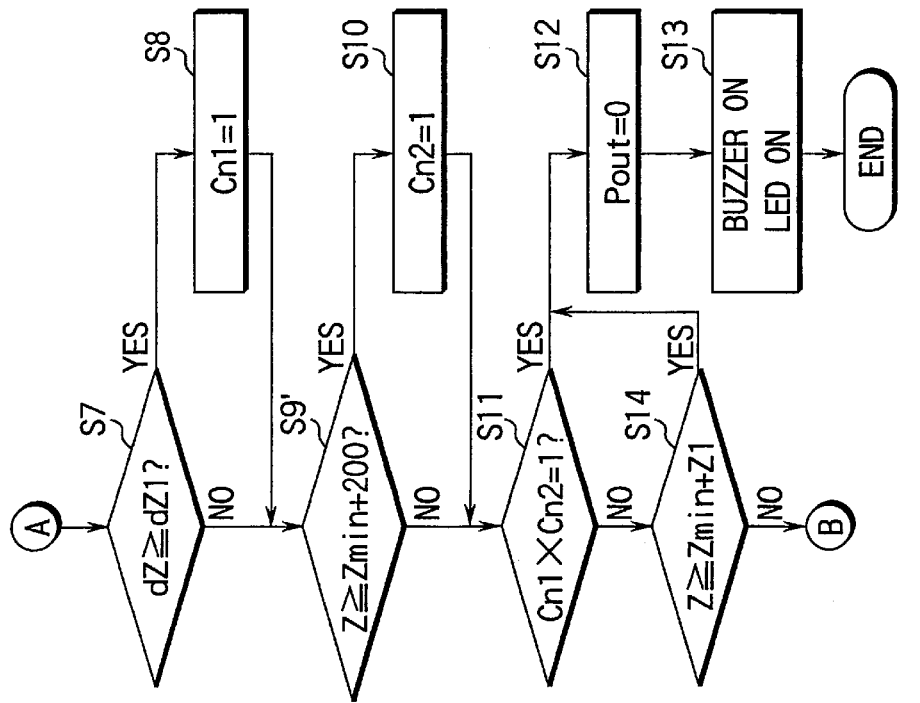
FIG. 6 is a flowchart illustrating the operation of the second embodiment of this invention.

A second embodiment of this invention will now be discussed. FIG. 6 is a flowchart illustrating the operation of the second embodiment. The steps in FIG. 6 are the same as those in FIG. 5 except that step S9 in FIG. 5 is replaced with step S9' where it is determined if the impedance Z is equal to or greater than the sum of the minimum impedance value Zmin and 200Ω. The second embodiment is therefore summarized as follows.
(1) The output is started and the impedance value Z is measured.
(2) The minimum impedance value Zmin is acquired.
(3) The output is stopped when the impedance value Z satisfies either one of the following conditions (a) and (b).
 (a) The rate of impedance change dZ has become equal to or greater than +300 Ω/sec at least once and the impedance value Z has become equal to or greater than the sum of the minimum impedance value Zmin and 200Ω.
 (b) The impedance value Z has become equal to or greater than the sum of the minimum impedance value Zmin and 500Ω.
(4) After the output is stopped in (3) above, the operator is informed through a buzzer sound or lit LED.

According to the above-described second embodiment, the same advantage can be obtained as that of the first embodiment.

Third Embodiment

Figure 7:
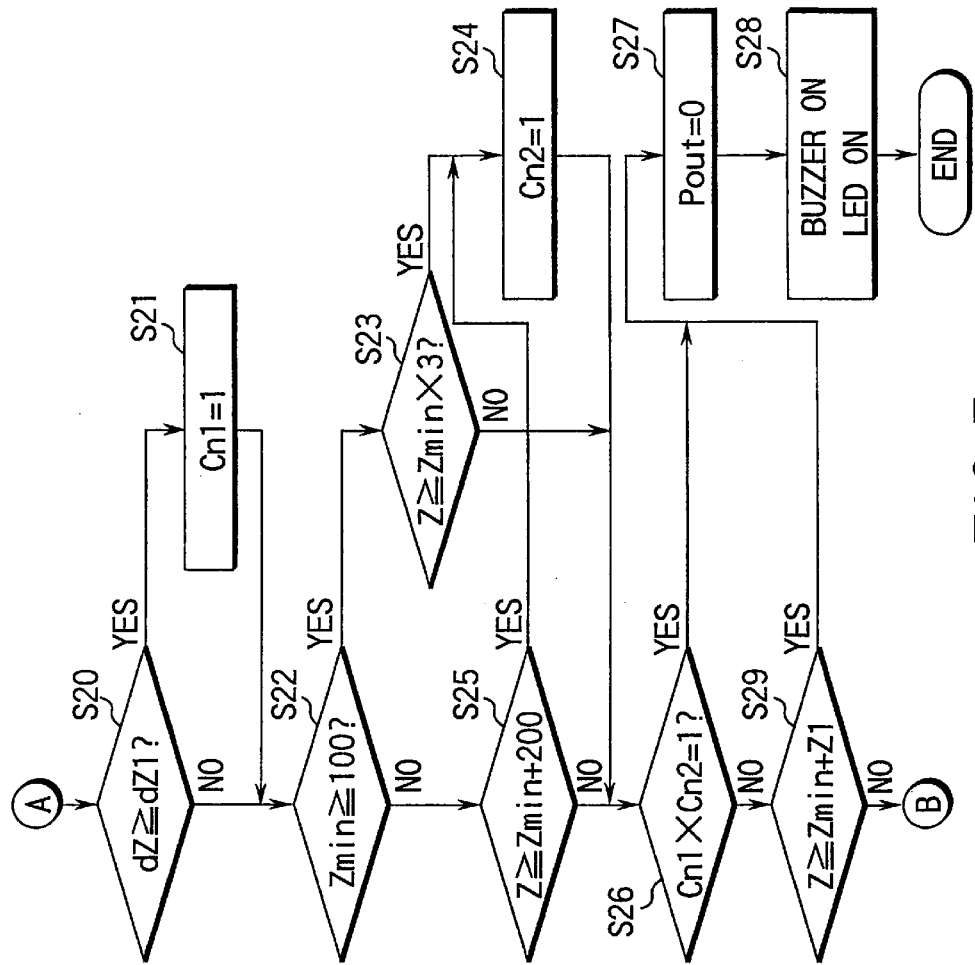
FIG. 7 is a flowchart illustrating the operation of the third embodiment of this invention.

A third embodiment of this invention will be discussed below. As the impedance value significantly varies depending on the types of tissues or the clamping state of forceps, a single decision condition is not enough to ensure a stable coagulation performance for every case. To cope with it, the third embodiment is characterized in that the condition for stopping the output is altered by the minimum impedance value. While the flowchart in FIG. 4 is commonly used to describe the operation of the third embodiment, a flowchart shown in FIG. 7 is used as a flowchart showing steps between A and B in FIG. 4. As the flowchart in FIG. 4 has already been discussed, only the flowchart in FIG. 7 will be discussed below.

First, it is determined if the calculated rate of impedance change dZ is equal to or greater than dZ1 (+300 Ω/sec in this example) (step S20). When the decision is "YES," "1" is substituted into the decision variable Cn1 (step S21) and the flow then moves to step S22. When the decision in step S20 is "NO," the flow immediately proceeds to step S22.

In step S22, it is determined if the minimum impedance value Zmin is equal to or greater than 100Ω. When the decision is "YES," it is then determined if the impedance Z is equal to or greater than the minimum impedance value Zmin multiplied by 3 (step S23). When the decision here is "YES," "1" is substituted into the decision variable Cn2 (step S24) and the flow then proceeds to step S26.

When the decision in step S22 is "NO," it is determined if the impedance Z is equal to or greater than the sum of the minimum impedance value Zmin and 200Ω (step S25). When the decision is "YES," the aforementioned step S24 is carried out before the flow advances to step S26. When the decision in step S25 is "NO," the flow immediately proceeds to step S26.

In step 526, it is determined if Cn1×Cn2 is equal to "1." When the decision is "YES," "0" is substituted into the output power Pout (step S27), and the informing section 14 outputs a sound (buzzer ON) from the speaker or turns on the LED (step S28) to inform the operator. This flow is then terminated.

When the decision in step S26 is "NO," it is determined if the impedance Z is equal to or greater than the sum of the minimum impedance value Zmin and the initial impedance value Zini (500Ω in this example) (step S29). When the decision is "YES," the flow goes to the aforementioned step S27. When the decision in step S29 is "NO," the flow returns to step S2 in FIG. 4.

The above-described third embodiment is summarized as follows.
(1) The output is started and the impedance value Z is measured.
(2) The minimum impedance value Zmin is acquired.
(3) The output is stopped when the impedance value Z satisfies either one of the following conditions (a) and (b).
Case A where the minimum impedance value Zmin is smaller than 100Ω:
  (a) The rate of impedance change dZ has become equal to or greater than +300 Ω/sec at least once and the impedance value Z has become equal to or greater than the sum of the minimum impedance value Zmin and 200Ω.
  (b) The impedance value Z has become equal to or greater than the sum of the minimum impedance value Zmin and 500Ω.
Case B where the minimum impedance value Zmin is equal to or greater than 100Ω:
  (a) The rate of impedance change dZ has become equal to or greater than +300 Ω/sec at least once and the impedance value Z has become equal to or greater than the minimum impedance value Zmin multiplied by 3.
  (b) The impedance value Z has become equal to or greater than the sum of the minimum impedance value Zmin and 500Ω.
(4) After the output is stopped in (3) above, the operator is informed through a buzzer sound or lit LED.

According to the above-described third embodiment, when the minimum impedance value Zmin is large, the range of a variation in impedance which matches with that variation size can be secured, and it is also possible to secure the variation range of the impedance of at least 200Ω, even if the minimum impedance value Zmin is small. This can ensure a more stable coagulation and hemostasis performance.

Fourth Embodiment

A fourth embodiment of this invention will now be discussed. In coagulating a thin tissue, as coagulation progresses, short-circuiting is likely to occur at a clamped part. In this case, the current locally flows to interfere with the progression of coagulation, but the current is not large enough to activate the current limiter, thus disabling detection of this short-circuited state. In this respect, the fourth embodiment is characterized in that the output is stopped upon detection of short-circuiting of the electrodes from the rate of impedance change or the impedance value. Specifically, the output is stopped when it is detected that the rate of impedance change dZ becomes equal to or smaller than −1000 Ω/sec as shown in FIG. 8, or that the impedance value Z becomes equal to or smaller than 5Ω as shown in FIG. 9.

The operation of the fourth embodiment will now be described referring to a flowchart in FIG. 10.

As the foot-operated switch 8 of the electrosurgical apparatus is switched ON (step S29), initialization is executed (step S30). In this initialization, the output power P1=40 W input by an operator via the setting input section 12 is set to the variable Pout associated with the output power. It is assumed that an initial rate of impedance change dZ2 has been set to −1000 Ω/sec and an initial impedance value Z2 has been set to 5Ω.

Next, it is determined if the foot-operated switch 8 has been switched OFF (step S31). When the decision is "YES," "0" is substituted into the output power Pout (step S32) after which this flow will be terminated.

When the decision in step S31 is "NO," the impedance Z and the rate of impedance change dZ are calculated (step S33). It is then determined if the calculated rate of impedance change dZ is equal to or smaller than the initial rate of impedance change dZ2 (−1000 Ω/sec in this example) (step S34). When the decision is "YES," "0" is substituted into the output power Pout (step S35), and the informing section 14 then outputs a sound (buzzer ON) from the speaker or turns on the LED (step S36) to inform the operator. This flow is then terminated.

When the decision in step S34 is "NO," it is determined if the impedance Z is equal to or smaller than the initial impedance value Z2 (5Ω in this example) (step S37). When the decision is "YES," the flow proceeds to the aforementioned step S35. When the decision in step S34 is "NO," the flow returns to step 31.

The above-described fourth embodiment is summarized as follows.
(1) The output is started and the impedance value Z and the rate of impedance change dZ are computed during outputting.
(2) When the impedance satisfies either one of the following conditions (a) and (b), which is considered as occurrence of short-circuiting, the buzzer is activated or the LED is turned on and then the output is stopped.
  (a) Rate of impedance change dZ≦−1000 Ω/sec.
  (b) Impedance value Z≦5Ω.

According to the above-described fourth embodiment, inadequate coagulation can be detected reliably by detecting short-circuiting during coagulation.

Fifth Embodiment

A fifth embodiment of this invention will be discussed below. The fifth embodiment is characterized by combining the automatic stop function at the end of coagulation in any one of the first to third embodiments with the short-circuiting detecting function of the fourth embodiment.

Figure 11:
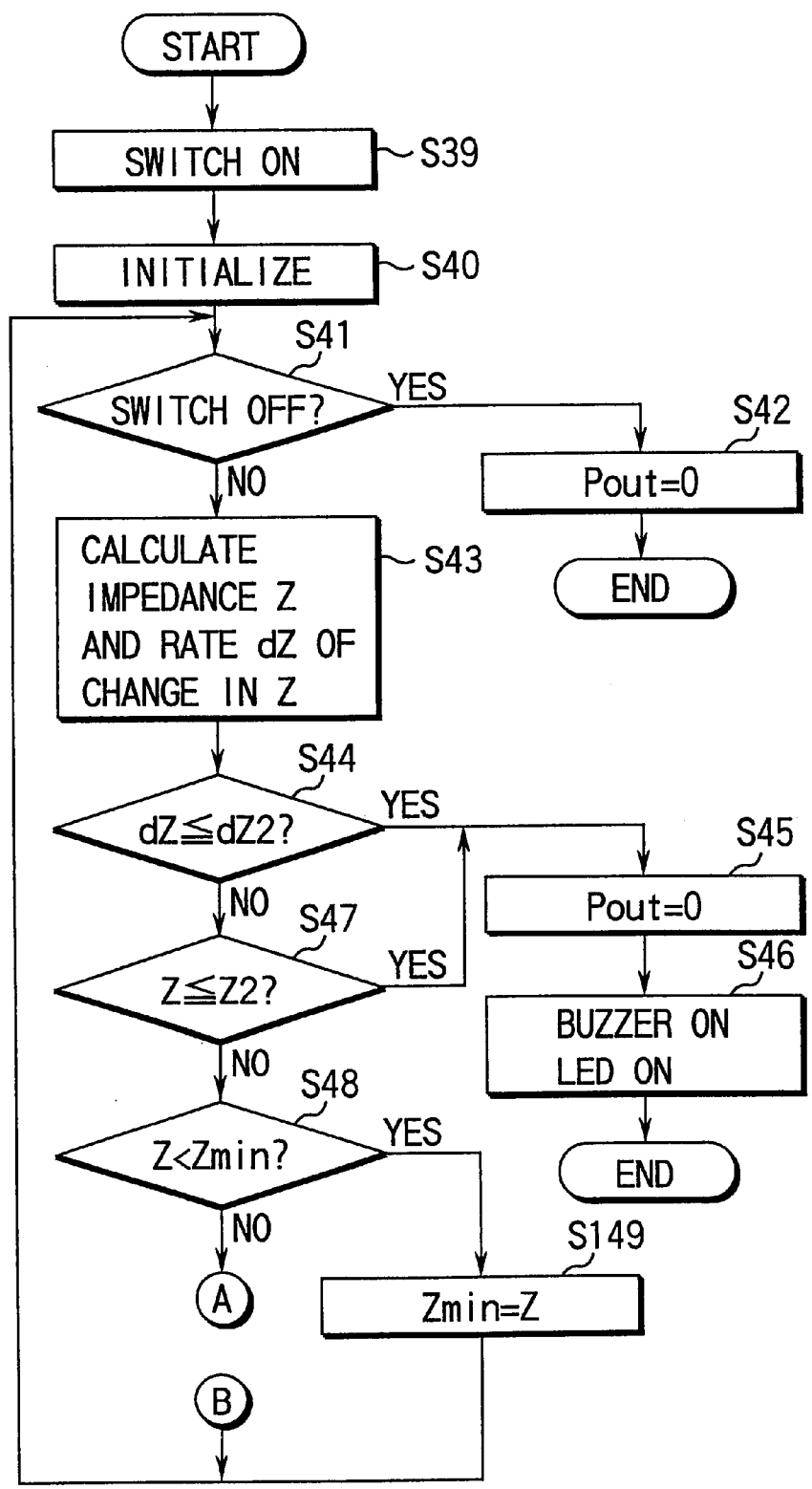
FIG. 11 is a flowchart illustrating the operation of a fifth embodiment of this invention.

FIG. 11 is a flowchart illustrating the operation of the fifth embodiment. This flowchart corresponds to the flowchart in FIG. 4 to which steps S44 to S47 that are carried out in the fourth embodiment are added. A flowchart between A and B in FIG. 11 may be any one of the flowcharts in FIGS. 5 to 7. As the other steps in FIG. 11 are the same as have been discussed above, their description will not be repeated.

According to this fifth embodiment, inadequate coagulation can be detected by detecting the occurrence of short-circuiting during a process of detecting the end of coagulation and stopping the output. This can realize an automatic coagulation stop function with a higher precision.

Sixth Embodiment

A sixth embodiment of this invention will now be described. Because the impedance value significantly varies depending on the types of tissues or the clamping state of forceps, a single load characteristic cannot provide a stable coagulation performance. To deal with this shortcoming, the sixth embodiment is characterized in that the output characteristic (load characteristic) and output power are altered based on the initial impedance value.

Figure 12:
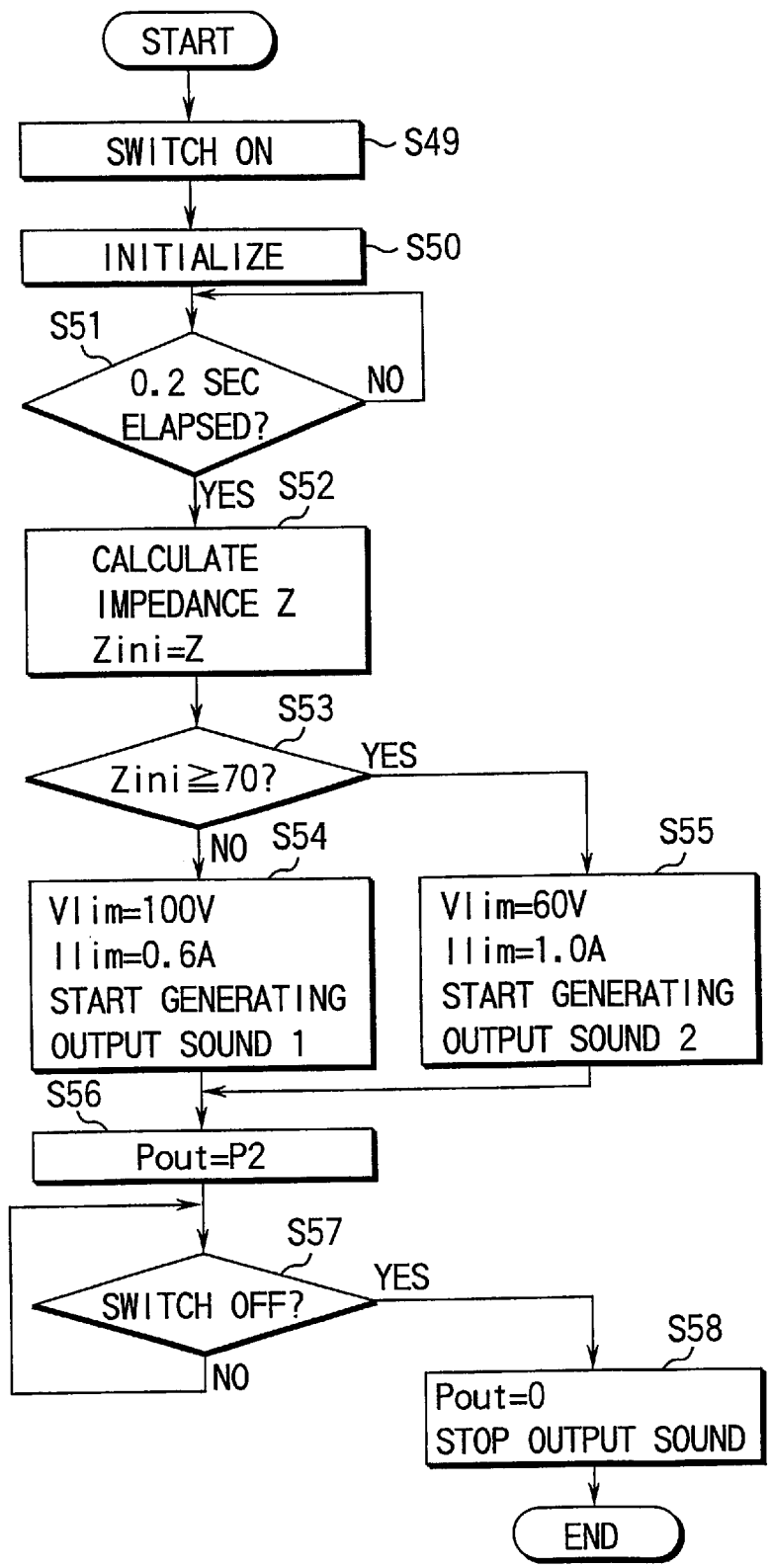
FIG. 12 is a flowchart illustrating the operation of a sixth embodiment of this invention.

FIG. 12 is a flowchart illustrating the operation of the sixth embodiment. When the foot-operated switch 8 of the electrosurgical apparatus is switched ON (step S49), initialization is implemented (step S50). In this initialization, the output power for measuring the impedance, P1=10 W, input by an operator via the setting input section 12, is substituted into the variable Pout associated with the output power. It is assumed that another output power P2=40 W has been set.

Next, it is determined if 0.2 sec has elapsed (step S51). When 0.2 sec has passed, the impedance Z is calculated and the calculated impedance Z is substituted into the initial impedance value Zini (step S52). It is then determined if this initial impedance value Zini is equal to or greater than 70Ω (step S53). When the decision is "NO," "100V" is substituted into a voltage limiter value Vlim and "0.6A" is substituted into a current limiter value Ilim. At the same time, the informing section 14 starts outputting a sound (output sound 1) from the speaker (step S54).

When the decision in step S53 is "YES," on the other hand, "60V" is substituted into the voltage limiter value Vlim and "1.0 A" into the current limiter value Ilim. At the same time, the informing section 14 starts outputting a sound (output sound 2) from the speaker (step S55). Then, the previously set output power P2 (40 W in this example) is substituted into the output power Pout (step S56), and it is then determined if the foot-operated switch 8 has been switched OFF (step S57). When it is determined that the foot-operated switch 8 has been switched OFF, "0" is substituted into the output power Pout and the informing section 14 stops outputting a sound from the speaker (step S58).

Next, the meaning of the changing the output characteristic is explained.

Figure 26:
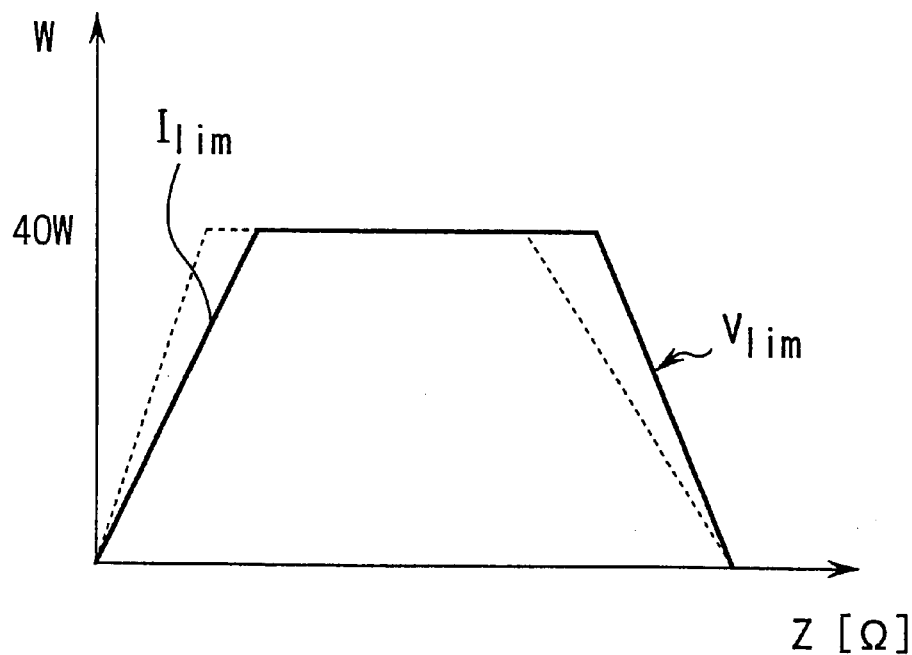
FIG. 26 is a diagram showing an output characteristic when an output voltage and an output current are limited.

FIG. 26 shows an output characteristic when an output voltage and an output current are limited. A rising portion of an output characteristic curve depends on the level of the current limitation (I lim) and a down portion of the output characteristic depends on the level of the voltage limitation (V lim). When the current limitation is large, a slope of a characteristic curve at the rising portion is steep. When the voltage limitation is high, a slope of the characteristic curve at the down portion is steep.

Figure 27:
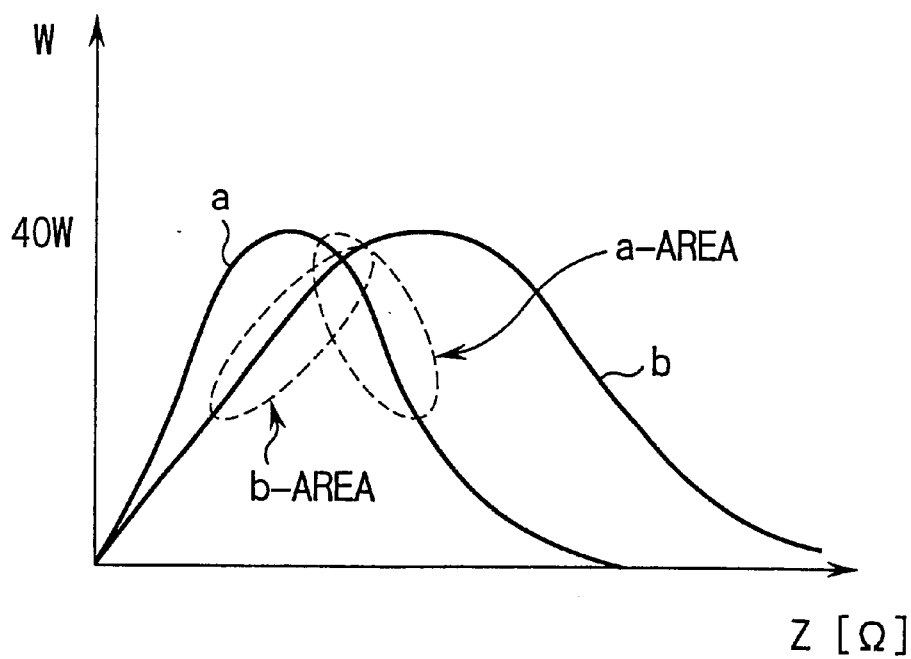
FIG. 27 is a diagram showing an output characteristic of power supply unit.

In this sixth embodiment, when the impedance measured at step S52 of FIG. 12 has proved to be high at step 53, the flow goes to step S55. In this case, the output characteristic of power supply unit shows a curve as shown by "a" in the FIG. 27. The power supply is mainly controlled in an "a-area" where the curve is decreasing. On the other hand, when the measured impedance is low, the flow goes to step S54. In this case, the output characteristic of power supply unit shows a curve as shown by "b" in the FIG. 27. The power supply is mainly controlled in a "b-area" where the curve is increasing. In this way, the current and voltage limitation are chosen so that the control is optimized.

The above-described sixth embodiment is summarized as follows.

(1) First, 10 W is output as the power for measuring the impedance and the impedance value after 0.2 sec is set as the initial value.
(2) The voltage limiter value and the current limiter value are set based on the initial impedance value Zini.
   (a) When Zini≧70Ω, the voltage limiter value Vlim= 60V and the current limiter value Ilim=1.0 A. (b) When Zini<70Ω, the voltage limiter value Vlim= 100V and the current limiter value Ilim=0.6 A.
   (c) The output is made with the set power value. At this time, different output sounds according to (a) and (b).

According to the above-described sixth embodiment, as the load characteristic is changed in accordance with individual tissues, a coagulation performance which matches with each tissue can be provided.

Seventh Embodiment

Figure 13:
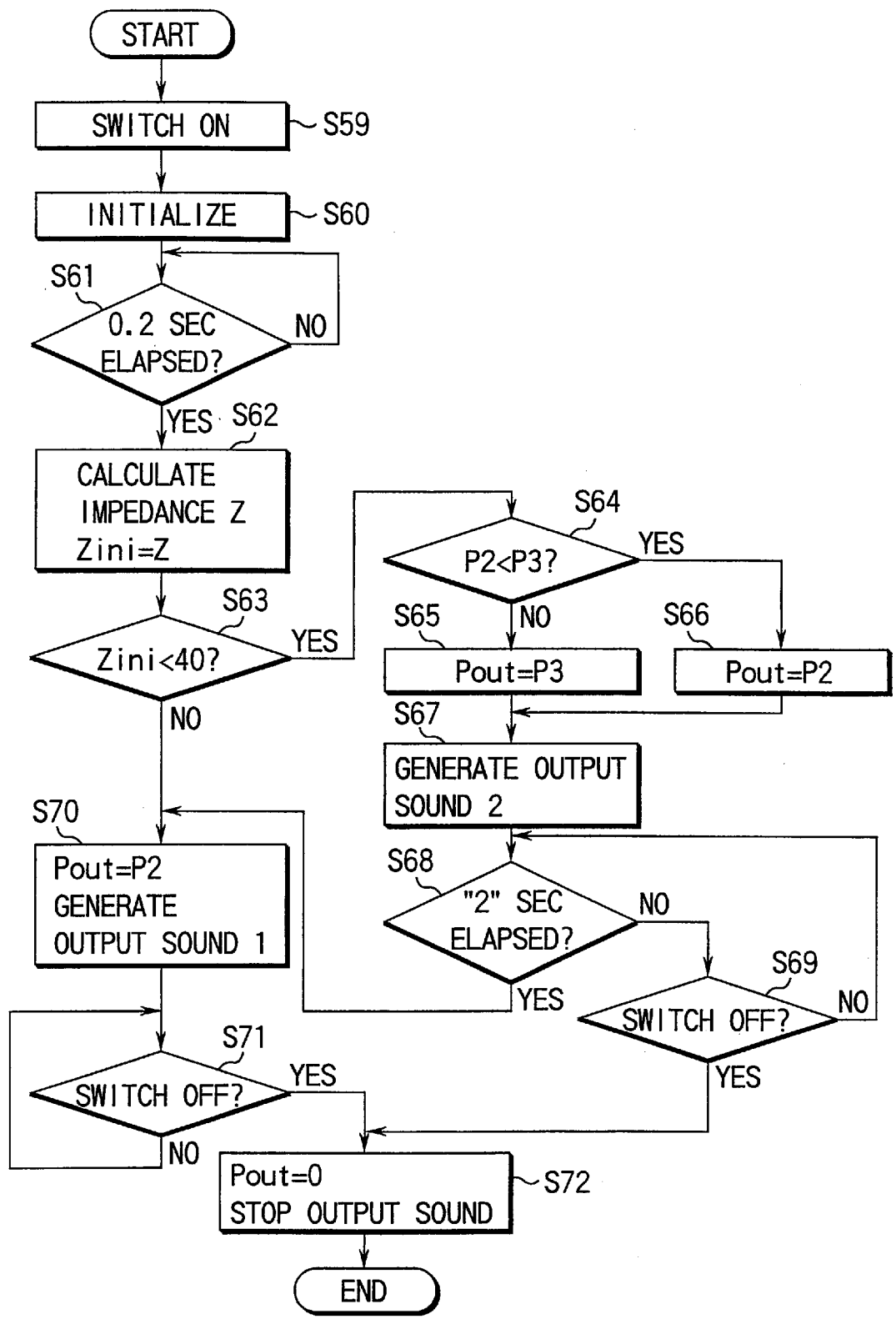
FIG. 13 is a flowchart illustrating the operation of a seventh embodiment of this invention.

A seventh embodiment of this invention will now be described with reference to FIG. 13. FIG. 13 is a flowchart for explaining the operation of the seventh embodiment. When the foot-operated switch 8 of the electrosurgical apparatus is switched ON (step S59), initialization is implemented (step S60). In this initialization, the output power for measuring the impedance, P1=10 W, input by an operator via the setting input section 12, is substituted into the variable Pout associated with the output power. It is assumed that other output powers P2=40 W and P3=20 W have been set.

Next, it is determined if 0.2 sec has elapsed (step S61). When 0.2 sec has passed, the impedance Z is calculated and the calculated impedance Z is substituted into the initial impedance value Zini (step S62). It is then determined if this initial impedance value Zini is equal to or greater than 40Ω (step S63). When the decision is "YES," it is determined if the set power P2 is lower than the set power P3 (step S64). When the decision is "NO," the value of P3 is substituted into the output power Pout (step S65) and the flow then proceeds to step S67. When the decision in step S64 is "YES," the value of P2 is substituted into the output power Pout (step S66) and the flow then proceeds to step S67.

In step S67, the informing section 14 starts outputting a sound (output sound 2 in this example) from the speaker. It is then determined if 2 sec has elapsed (step S68). When the decision is "NO," it is then determined if the foot-operated switch 8 has been switched OFF (step S69). When the decision here is "NO," the flow returns to step S68, and when the decision is "YES," the flow proceeds to step S72.

When the decision in step S63 is "NO" or the decision in step S68 is "YES," on the other hand, the flow goes to step S70 to substitute the initial power P2 (40 W in this example) into the output power Pout. At the same time, the informing section 14 starts outputting a sound (output sound 1 in this example) from the speaker. Then, it is determined if the foot-operated switch 8 is OFF (step S71). When it is determined that the foot-operated switch 8 is OFF, the flow proceeds to step S72. In step S72, "0" is substituted into the output power Pout and the sound output is stopped, then this flow is terminated.

The above-described seventh embodiment is summarized as follows.

(1) First, 10 W is output as the power for measuring the impedance and the impedance value after 0.2 sec is set as the initial value.
(2) When the initial impedance value Zini is less than 40Ω, the output is limited to 20 W or lower for 2 seconds after the measuring has completed. When the set power is equal to or greater than 20 W, 20 W is output, and when the set power is less than 20 W, the set power is output. After 2 seconds, the set power is output.
(3) When the initial impedance value Zini is equal to or greater than 40Ω, the set power is output from the beginning.
(4) During output restriction in (2), the output sound 2 different from the normal output sound 1 is generated.

According to the above-described seventh embodiment, the first output is limited low for a low-impedance tissue, so that outputs which match with the individual tissues can be made using the same load characteristic. This can provide the coagulation performance suitable for each tissue.

Although the output is stopped when a predetermined impedance condition is met in this embodiment, this is not restrictive and the output may of course be reduced.

The above-described first to seventh embodiments can provide electrosurgical apparatuses which can more reliably stop the output at the end of coagulation to avoid overburning.

Eighth Embodiment

An eighth embodiment is characterized in that the current condition for the output control or stopping the output (automatic stop) is changed in accordance with the coagulation level set by a user.

Figure 14:
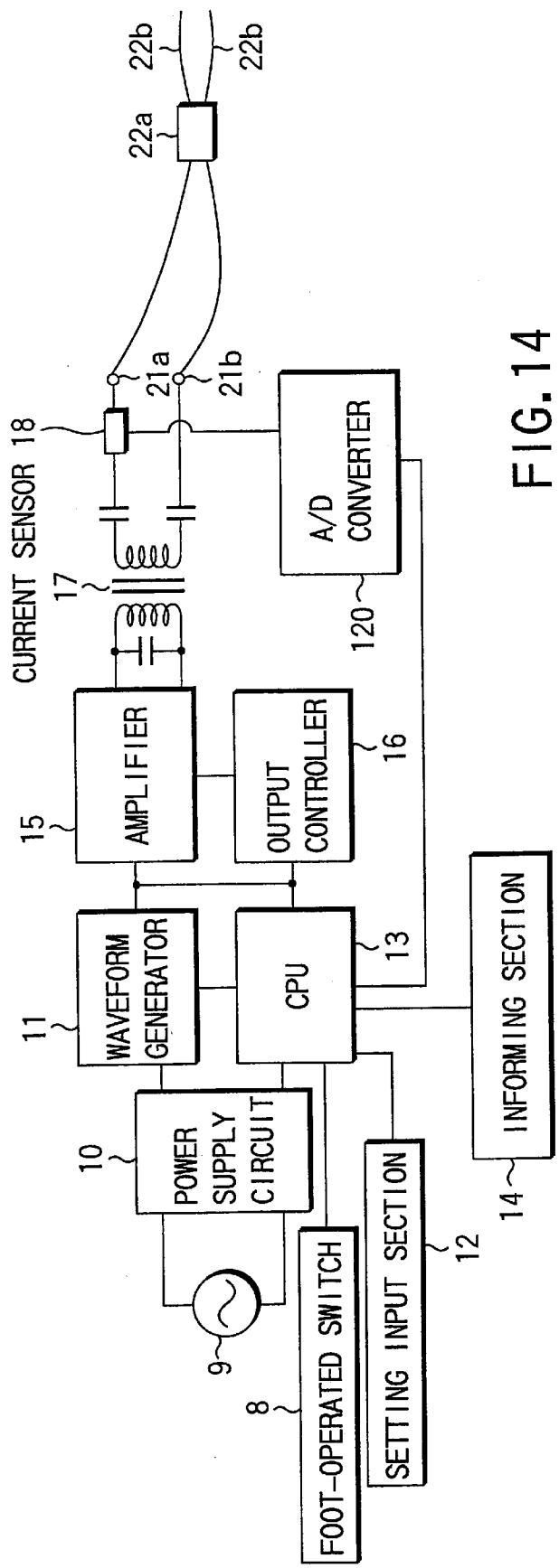
FIG. 14 is a diagram illustrating the internal structure of an electrosurgical apparatus according to an eighth embodiment of this invention.

FIG. 14 is a diagram illustrating the internal structure of an electrosurgical apparatus according to the eighth embodiment. This structure is quite the same as the one shown in FIG. 1 except that the voltage sensor 19 in the structure in FIG. 1 is eliminated and instead of the impedance calculator 20, an A/D converter 120 is connected to the current sensor 18.

Although the bipolar instrument is illustrated as an instrument in FIG. 14, the monopolar instrument 23 with the monopolar electrode 23a may be used instead as shown in FIG. 2. In this case, the feedback electrode 25 is connected to the terminal 21b via the feedback line. The A/D converter 120 is connected between the output of the current sensor 18 and the CPU 13. The CPU 13 is further connected to the foot-operated switch 8, the setting input section 12 and the informing section 14.

In the eighth embodiment, the high-frequency output is controlled by controlling the amplifier 15 by the CPU 13 and the output controller 16 as the control section.

Figure 15:
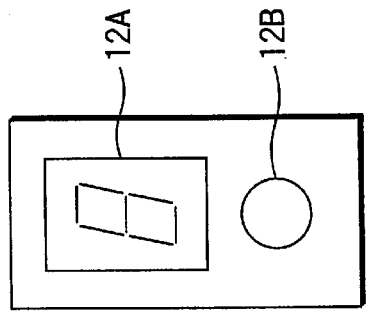
FIG. 15 is a diagram showing the structure of a setting input section 12.

FIG. 15 is a diagram showing the structure of the setting input section 12, which has a setting switch 12B for permitting the user to set a coagulation level and a coagulation level display section 12A for displaying the set coagulation level. Every time the setting switch 12B is depressed, the coagulation level is displayed on the coagulation level display section 12A while changing in the order of 1→2→3→4→1 and a current value Istop=0.6 A, 0.5 A, 0.4 A or 0.2A for stopping the output is set in association with each coagulation level 1 2, 3 or 4 set.

Figure 16:
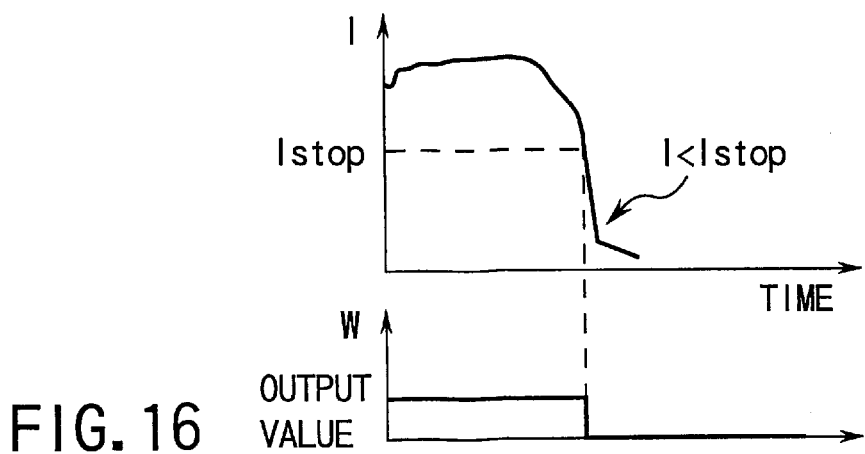
FIG. 16 is a diagram showing the relationship between the characteristic of a high-frequency current (I) and the output of a power supply circuit 10.

FIG. 16 shows the relationship between the characteristic of a high-frequency current (I) and the out put of the power supply circuit 10 and shows that the output of the amplifier 15 is stopped when the current condition for stopping the output is met.

Figure 17:
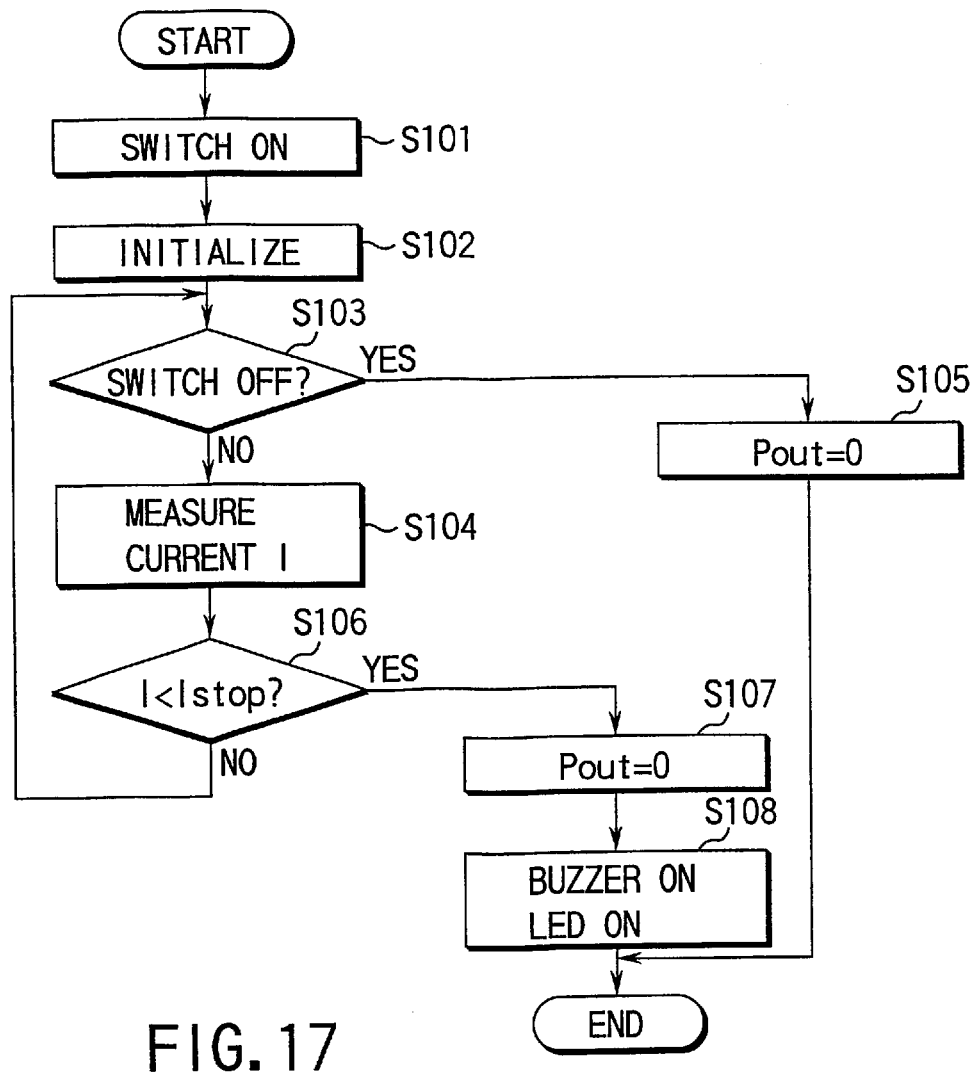
FIG. 17 is a diagram for explaining the operation of the eighth embodiment of this invention.

The operation of the eighth embodiment will be explained below referring to a flowchart in FIG. 17.

As the foot-operated switch 8 for initiating the steady power output from the electrosurgical apparatus is switched ON (step S101), initialization is executed (step S102). In this initialization, the output power P1=40 W input by a user via the setting input section 12 is substituted into the variable Pout associated with the output power, a coagulation level is set, and the current value Istop as the current condition for stopping the output is set. The set values input by the user are stored in a memory section in the CPU 13 to be used in a next surgery.

Then, it is determined if the foot-operated switch 8 has been switched OFF (step S103). When the foot-operated switch 8 has been switched OFF, "0" is substituted into the output power Pout (step S105) to stop the high-frequency output, and then this flow is terminated. When the foot-operated switch 8 has not been switched OFF, the current value I detected by the current sensor 18 is measured (step S104) and it is then determined if the measured current value I is lower than the set current value Istop (step S106). When the decision is "NO," the flow returns to step S103. When the current value I measured after a predetermined time is lower than the set current value Istop, the decision in step S106 becomes "YES" so that the flow proceeds to step S107 where "0" is substituted into the output power Pout to stop the high-frequency output. At the same time, the informing section 14 outputs a sound (buzzer ON) from the speaker or turns on the LED (step S108) to inform the user after which this flow will be terminated.

According to the above-described eighth embodiment, the coagulation level in automatic stop mode can be changed in accordance with the user's selection by altering the current condition for detecting the end of coagulation.

Ninth Embodiment

A ninth embodiment of this invention will be discussed below referring to the accompanying drawings. The ninth embodiment is characterized in that the voltage condition for stopping the output is changed in accordance with the coagulation level set by a user.

Figure 18:
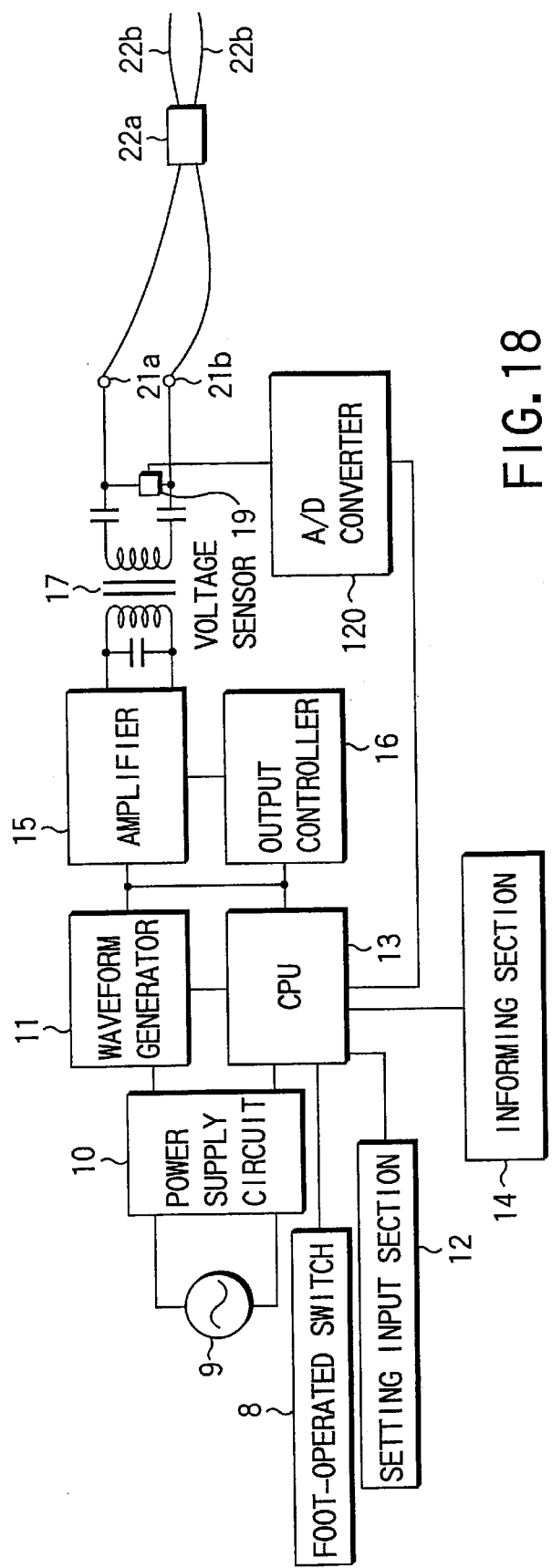
FIG. 18 is a diagram illustrating the internal structure of an electrosurgical apparatus according to a ninth embodiment of this invention.

FIG. 18 is a diagram illustrating the internal structure of an electrosurgical apparatus according to the ninth embodiment. This structure is basically the same as that of the eighth embodiment except for the voltage sensor 19 provided in place of the current sensor 18.

According to the ninth embodiment, the voltage condition can be set by using the structure of the setting input section 12 as shown in FIG. 15. In this case, however, a voltage value Vstop=60V, 90V, 120V or 150V for stopping the output is set in association with each coagulation level 1, 2, 3 or 4 set.

Figure 19:
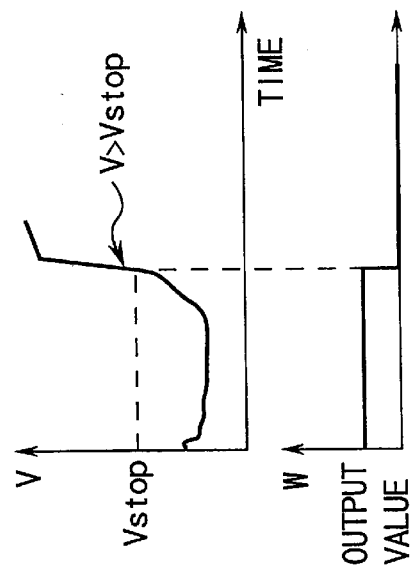
FIG. 19 is a diagram showing the relationship between the characteristic of a high-frequency output (V) and the output of the power supply circuit 10.

FIG. 19 shows the relationship between the characteristic of a high-frequency voltage (V) and the output of the power supply circuit 10 and shows that the output of the amplifier 15 is stopped when the voltage condition for stopping the output is met.

Figure 20:
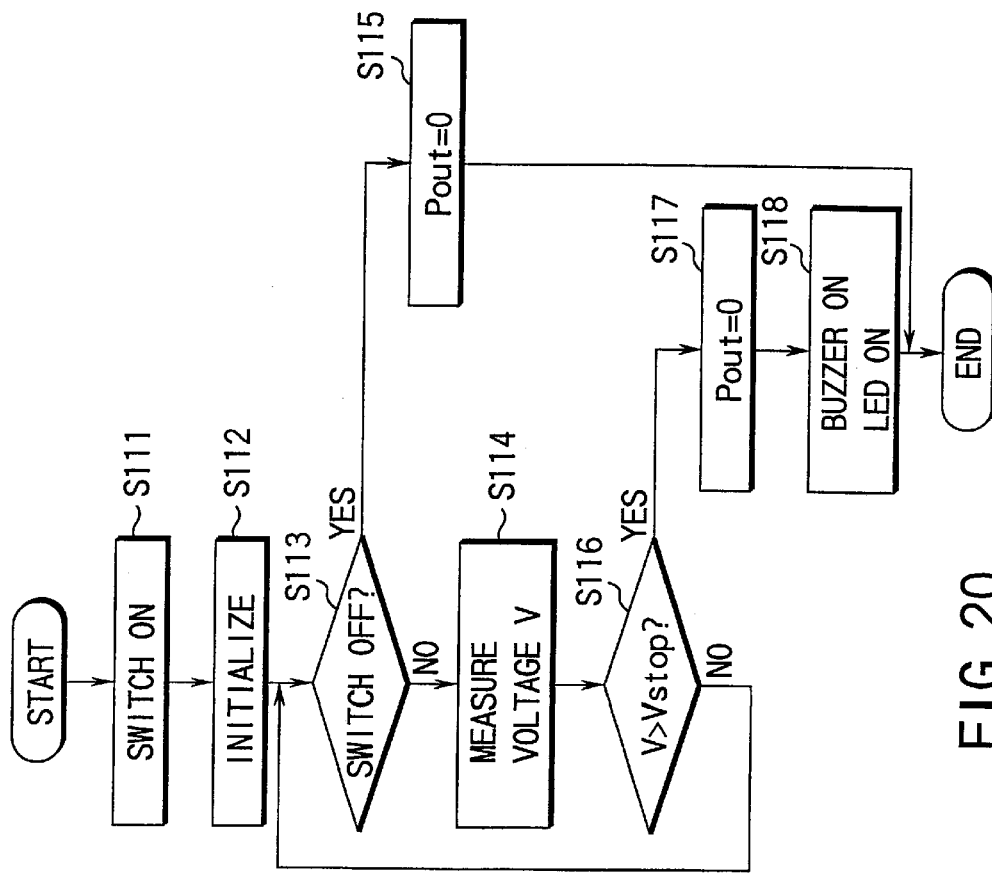
FIG. 20 is a diagram for explaining the operation of the ninth embodiment of this invention.

The operation of the ninth embodiment will now be discussed referring to a flowchart in FIG. 20.

As the foot-operated switch 8 for initiating the steady power output from the electrosurgical apparatus is switched ON (step S111), initialization is executed (step S112). In this initialization, the output power P1=40 W input by a user via the setting input section 12 is substituted into the variable Pout associated with the output power, a coagulation level is set, and the voltage value Vstop as the voltage condition for stopping the output is set.

Then, it is determined if the foot-operated switch 8 has been switched OFF (step S113). When the foot-operated switch 8 has been switched OFF, "0" is substituted into the output power Pout (step S115) to stop the high-frequency output, and then this flow is terminated. When the foot-operated switch 8 has not been switched OFF, the voltage value V detected by the voltage sensor 19 is measured (step S114) and it is then determined if the measured voltage value V is higher than the set voltage value Vstop (step S116). When the decision is "NO," the flow returns to step S113. When the voltage value V measured after a predetermined time is exceeds the set voltage value Vstop, the decision in step S116 becomes "YES" so that the flow proceeds to step S117 where "0" is substituted into the output power Pout to stop the high-frequency output. At the same time, the informing section 14 outputs a sound (buzzer ON) from the speaker or turns on the LED (step S118) to inform the user after which this flow will be terminated.

According to the above-described ninth embodiment, the coagulation level in automatic stop mode can be changed in accordance with the user's selection by altering the voltage condition for detecting the end of coagulation.

Tenth Embodiment

A tenth embodiment of this invention will be discussed below referring to the accompanying drawings. The tenth embodiment is characterized in that the impedance condition for stopping the output is changed in accordance with the coagulation level set by a user.

The internal structure of an electrosurgical apparatus according to the tenth embodiment is the same as the above-described structure shown in FIG. 1. This structure is the combination of the abovedescribed structures shown in FIGS. 14 and 18 except for the impedance calculator 20 provided in place of the A/D converter 120.

This tenth embodiment can likewise set the impedance condition by using the structure of the setting input section 12 as shown in FIG. 15. In this case, however, three variables P_dZ (rate of impedance change (Ω/sec)), P_mZ (multiplier constant) and P_Z (impedance value (Ω)) are used as the impedance conditions to be set for stopping the output, and are determined as follows in association with each coagulation level 1, 2, 3 or 4 set.

coagulation level 1: P_dZ=300, P_mZ=3, P_Z=300
coagulation level 2: P_dZ=400, P_mZ 3, P_Z 400
coagulation level 3: P_dZ=500, P_mZ=4, P_Z=500
coagulation level 4: P_dZ=600, P_mZ=4, P_Z=600

FIG. 3 shows the relationship between the characteristic of the impedance (Z) and the output of the power supply circuit 10 and shows that the output of the amplifier 15 is stopped when the impedance condition is met.

Figure 21:
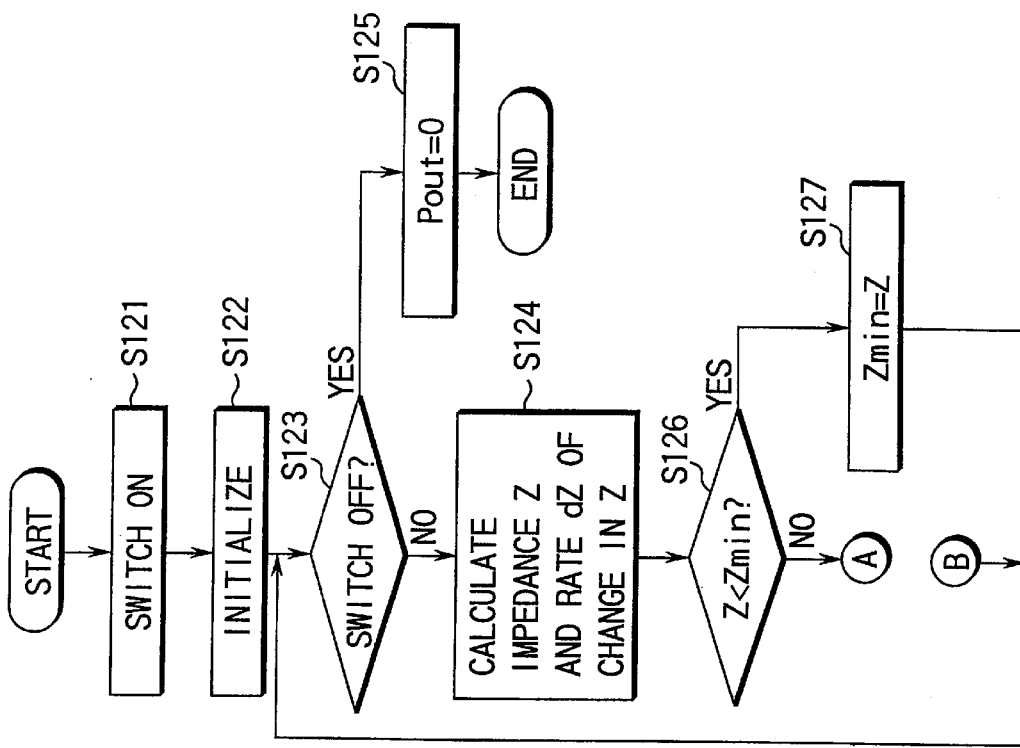
FIG. 21 is a diagram (part 1) for explaining the operation of a tenth embodiment of this invention.

The operation of the tenth embodiment will now be discussed referring to a flowchart in FIG. 21.

As the foot-operated switch 8 for starting the steady power output from the electrosurgical apparatus is switched ON (step S121), initialization is carried out (step S122). In this initialization, the output power P1=40 W input by a user via the setting input section 12 is set to a variable Pout associated with the output power and 10 KΩ is set to a variable Zmin associated with the minimum impedance value. Further, P_dZ, P_mZ and P_Z set by the user in association with the coagulation level are set. In addition, the decision variable Cn1=0 and decision variable Cn2=0 are set.

Then, it is determined if the foot-operated switch 8 has been switched OFF (step S123). When the foot-operated switch 8 has been switched OFF, "0" is set to the output power Pout (step S125) to stop the high-frequency output after which this flow will be terminated. When the foot-operated switch 8 has not been switched OFF, the impedance Z and the rate of impedance change dZ are calculated (step S124). Next, it is determined if the calculated impedance Z is smaller than the minimum impedance value Zmin (step S126). When the decision is "YES," the calculated impedance Z is substituted into the minimum impedance value Zmin (step S127) and then the flow returns to step S123.

Figure 22:
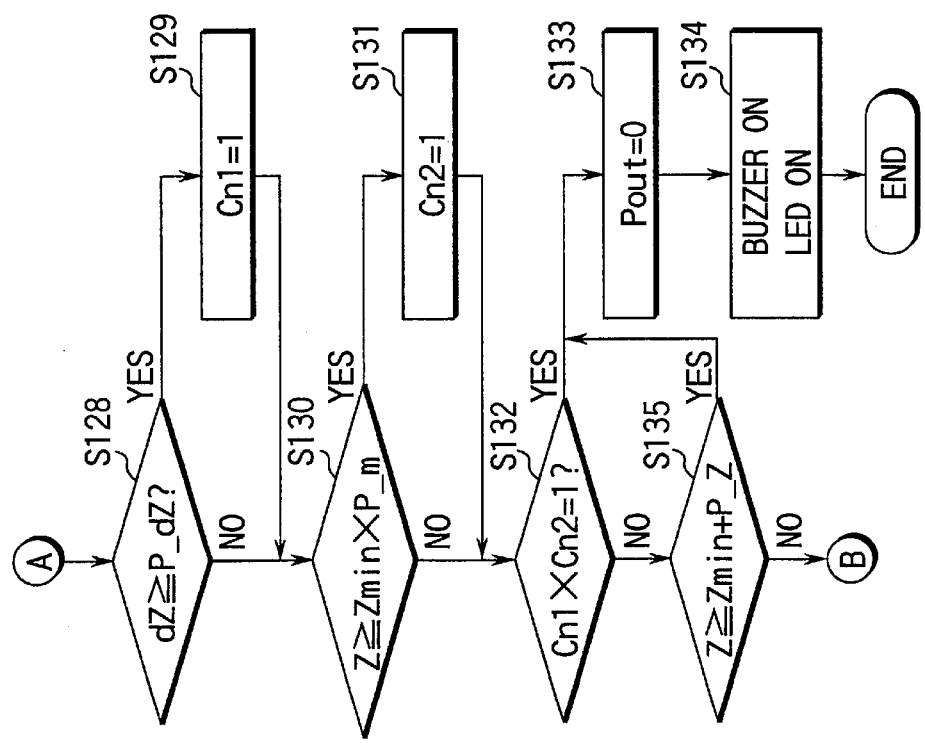
FIG. 22 is a diagram (part 2) for explaining the operation of the tenth embodiment of this invention.

When the decision in step S126 is "NO," on the other hand, the flow proceeds to step S128 in FIG. 22 to determine if the calculated rate of impedance change dZ is equal to or greater than P_dZ. When the decision is "YES," "1" is substituted into the decision variable Cn1 (step S129) and the flow then goes to step S130. When the decision in step S128 is "NO," the flow immediately proceeds to step S130.

In step S130, it is determined if the impedance Z is equal to or greater than the minimum impedance value Zmin multiplied by the multiplier constant P_m. When the decision is "YES," "1" is substituted into the decision variable Cn2 (step S131) and the flow then proceeds to step S132. When the decision in step S130 is "NO," the flow immediately proceeds to step S132.

In step S132, it is determined if Cn1×Cn2 is equal to "1." When the decision is "YES," "0" is substituted into the output power Pout (step S133) to stop the high-frequency output, and the informing section 14 outputs a sound (buzzer ON) from the speaker or turns on the LED (step S134) to inform the user. This flow is then terminated.

When the decision in step S132 is "NO," it is determined if the impedance Z is equal to or greater than the sum of the minimum impedance value Zmin and the initial impedance value P_Z (step S135). When the decision is "YES," the processes starting at the aforementioned step S133 are executed. When the decision in step S135 is "NO," the flow returns to step S123 in FIG. 21.

As apparent from the above, the tenth embodiment stops the high-frequency output when the impedance satisfies either one of the following conditions (a) and (b).
 (a) The rate of impedance change dZ has become equal to or greater than P_dZ at least once and the impedance value Z has become equal to or greater than the product of the minimum impedance value Zmin and P m.
 (b) The impedance value Z has become equal to or greater than the sum of the minimum impedance value Zmin and P_Z.

According to the above-described tenth embodiment, the coagulation level in automatic stop mode can be changed in accordance with the user's selection by altering the impedance condition for detecting the end of coagulation.

Eleventh Embodiment

An eleventh embodiment of this invention will be discussed below referring to the accompanying drawings. The eleventh embodiment is characterized in that the delay time for stopping the output is changed in accordance with the coagulation level set by a user.

The internal structure of an electrosurgical apparatus according to the eleventh embodiment is the same as that of the tenth embodiment. The eleventh embodiment can likewise use the structure of the setting input section 12 as shown in FIG. 15 to set the delay time for stopping the output. In this case, however, the delay time for stopping the output is set to T=0 sec, 1 sec, 2 sec or 3 sec in association with each coagulation level 1, 2, 3 or 4 set. P_dZ (rate of impedance change), P_mZ (multiplier constant) and P_Z (impedance value) as the impedance conditions are fixed to P_dZ=300 (Ω/sec), P_mZ=3 and P_Z=500 (Ω).

Figure 23:
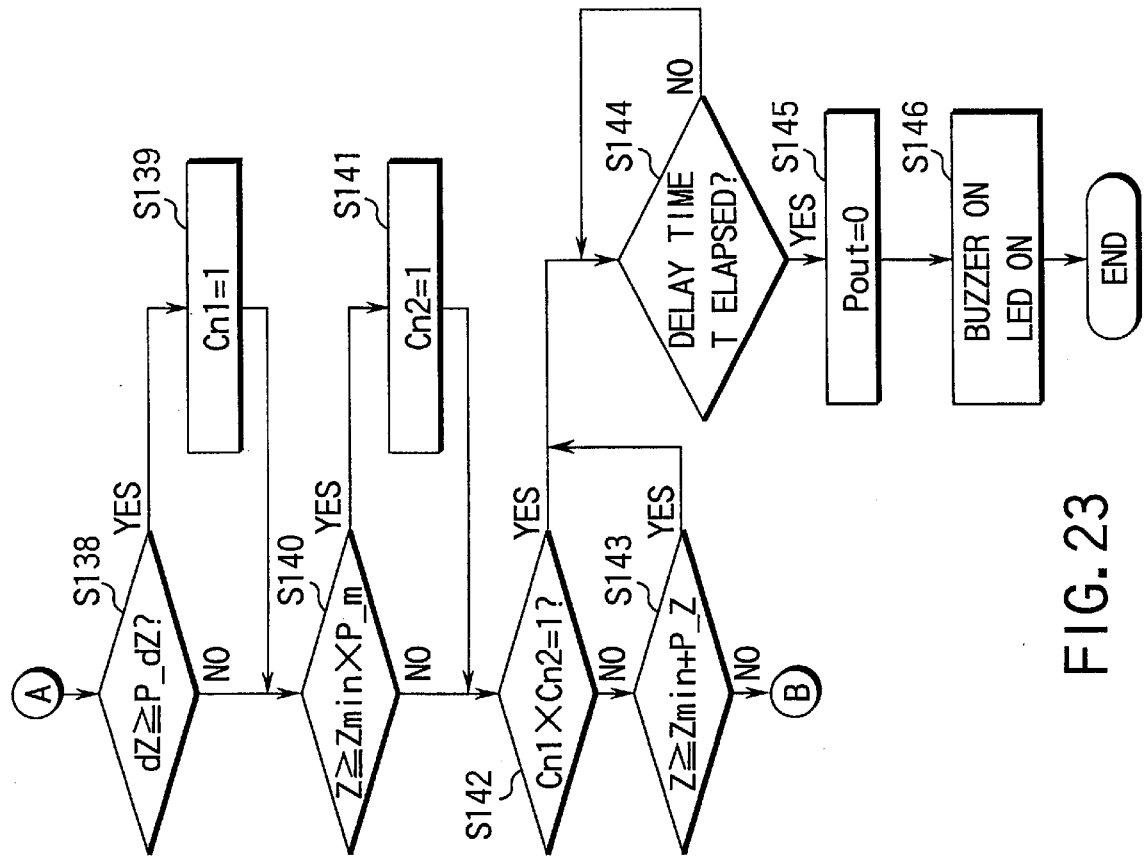
FIG. 23 is a diagram for explaining the operation of an eleventh embodiment of this invention.

The operation of the eleventh embodiment of this invention will be discussed below. While the flowchart in FIG. 21 is commonly used to describe the operation of the eleventh embodiment, the delay time T is set in the initialization in step S122. The difference lies in that a flowchart shown in FIG. 23 is used in the eleventh embodiment as a flowchart showing steps between A and D in FIG. 21. As the flowchart in FIG. 21 has already been discussed, only the flowchart in FIG. 23 will be discussed below. First, it is determined in step S138 if the calculated rate of impedance change dZ is equal to or greater than P_dZ (300 Ω/sec in this example). When the decision is "YES," "1" is substituted into the decision variable Cn1 (step S139) and the flow then moves to step S140. When the decision in step S138 is "NO," the flow immediately proceeds to step S140.

In step S140, it is determined if the impedance Z is equal to or greater than the minimum impedance value Zmin multiplied by the multiplier constant P_m (3 in this example). When the decision is "YES," "1" is substituted into the decision variable Cn2 (step S141) and the flow then proceeds to step S142. When the decision in step S140 is "NO," the flow immediately proceeds to step S142.

In step S142, it is determined if the product of Cn1 and Cn2 is equal to "1." When the decision is "YES," the flow proceeds to step S144 to wait for the delay time T to elapse. When the delay time T elapses, the decision in step S144 becomes "YES" and the flow then goes to step S145. In step S145, "0" is substituted into the output power Pout to stop the high-frequency output, and the informing section 14 outputs a sound (buzzer ON) from the speaker or turns on the LED (step S146) to inform the user. This flow is then terminated.

When the decision in step S142 is "NO," the flow proceeds to step S143 to determine if the impedance Z is equal to or greater than the sum of the minimum impedance value Zmin and the initial impedance value P_Z (500Ω in this example). When the decision is "YES," the processes starting at the aforementioned step S144 are executed. When the decision in step S143 is "NO," the flow returns to step S123 in FIG. 21.

As apparent from the above, the eleventh embodiment stops the high-frequency output when the delay time T elapses after the impedance satisfies either one of the following conditions (a) and (b).

(a) The rate of impedance change dZ has become equal to or greater than +300 Ω/sec at least once and the impedance value Z has become equal to or greater than the minimum impedance value Zmin multiplied by 3.

(b) The impedance value Z has become equal to or greater than the sum of the minimum impedance value Zmin and 500 Ω.

The above-described eleventh embodiment has such an effect that there is no variation in detection due to the same threshold value (current, voltage, impedance or the like) used in addition to changing the coagulation level in automatic stop mode in accordance with the user's selection of the delay time.

Twelfth Embodiment

Figure 24:
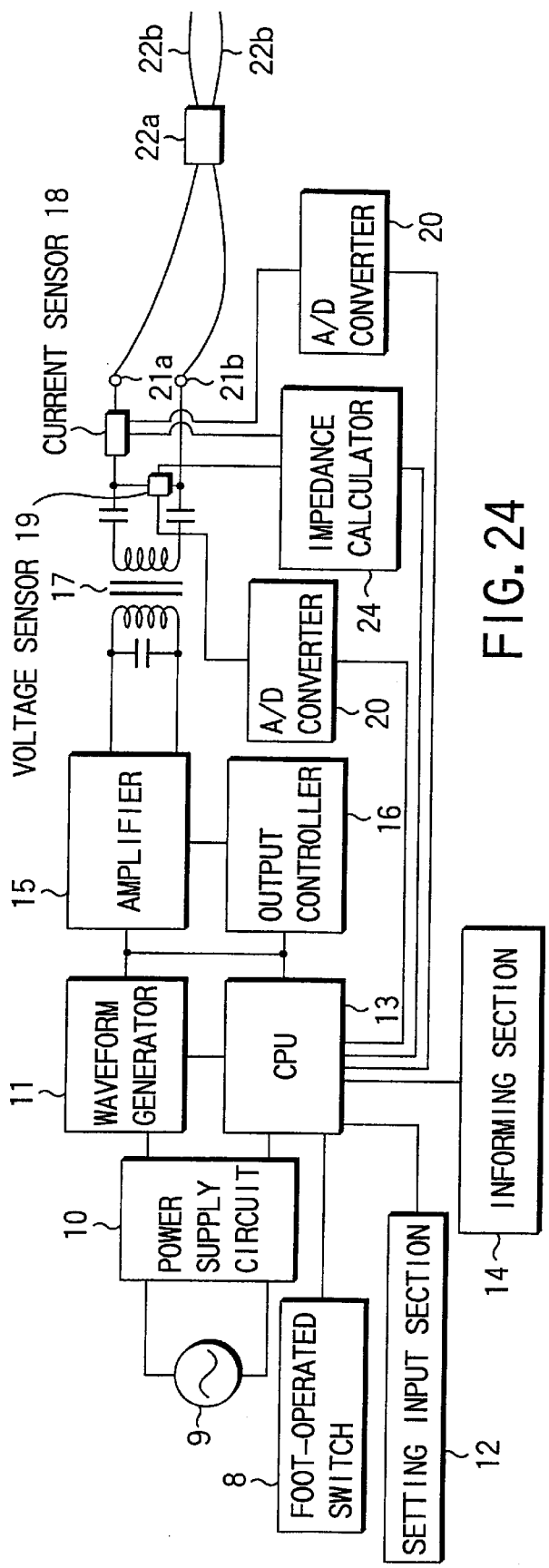
FIG. 24 is a diagram illustrating the internal structure of an electrosurgical apparatus according to a twelfth embodiment of this invention.
Figure 25:
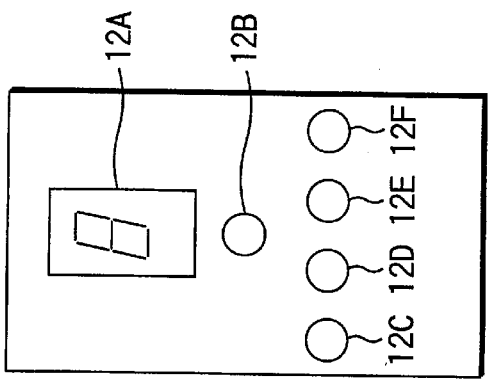
FIG. 25 is a diagram showing the structure of a setting input section 12 according to the twelfth embodiment of this invention.

A twelfth embodiment of this invention will be discussed below. The twelfth embodiment is the combination of the eighth to eleventh embodiments, and FIG. 24 illustrates the internal structure of an electrosurgical apparatus according to the twelfth embodiment. The setting input section 12 in this case takes a structure as shown in FIG. 25, so that a user can designate an appropriate output stop condition by depressing a one of a current select button 12C, a voltage select button 12D, an impedance select button 12E and a delay-time select button 12F. The user can then set the coagulation level by depressing the setting switch 12B. After the above setting is made, a sequence of processes will be carried out according to each setting and each of the combined embodiments.

The above-described twelfth embodiment can set the desired output stop condition.

The above-described eighth to twelfth embodiments can provide electrosurgical apparatuses which are able to change the coagulation level according to a user's selection by changing the condition for detecting the end of coagulation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electrosurgical apparatus for supplying high-frequency power from a high-frequency power supply unit to an instrument placed in association with an organic tissue to dissect or coagulate said organic tissue, said electrosurgical apparatus comprising:

an impedance calculating section for calculating an impedance value or said organic tissue;

a rate-of-impedance-change calculating section for calculating a rate of impedance change of said organic tissue based on said impedance value calculated by said impedance calculating section; and a control section for controlling a high-frequency output of said high-frequency power supply unit based on a predetermined condition provided by an evaluation of both said impedance value calculated by said impedance calculating section and said rate of impedance change calculated by said rate-of-impedance-change calculating section;

wherein said impedance calculating section acquires said impedance value by measuring a voltage and a current in said high-frequency output, and said control section detects a short-circuited state between electrodes based on said impedance value and wherein said control section detects said short-circuited state when an absolute value of a negative rate of impedance change becomes equal to or greater than a first predetermined value or said impedance value becomes equal to or smaller than a second predetermined value.

2. The electrosurgical apparatus according to claim 1, wherein said control section controls said high-frequency output of said high-frequency power supply unit when either a condition that said rate of impedance change has become equal to or greater than a first predetermined value at least once and said impedance value has become equal to or greater than a second predetermined value acquired from a function of a predetermined minimum impedance value, or a condition that said impedance value becomes equal to or greater than a sum of said minimum impedance value and a third predetermined value is satisfied.

3. The electrosurgical apparatus according to claim 2, said function of said minimum impedance value includes two different functions and they are used interchangebly in accordance with said minimum impedance value.

4. The electrosurgical apparatus according to claim 1, wherein said control section stops said high-frequency output upon detection of said short-circuited state.

5. A control apparatus, connected to an electrosurgical apparatus having an instrument for performing a predetermined treatment on an organic tissue and a high-frequency power supply unit for supplying high-frequency power for treating said organic tissue to said instrument, for controlling said high-frequency power output from said high-frequency power supply unit, said control apparatus comprising:

an impedance calculating section for calculating an impedance value of said organic tissue;

a rate-of-impedance-change calculating section for calculating a rate of impedance change of said organic tissue based on said impedance value calculated by said impedance calculating section; and a control section for controlling a high-frequency output of said high-frequency power supply unit based on a predetermined condition provided by combining said impedance value calculated by said impedance calculating section with said rate of impedance change calculated by said rate-of-impedance-change calculating section;

wherein said impedance calculating section acquires said impedance value by measuring a voltage and a current in said high-frequency output, and said control section detects a short-circuited state between electrodes based on said impedance value and wherein said control section detects said short-circuited state when an absolute value of a negative rate of impedance change becomes equal to or greater than a first predetermined value or said impedance value becomes equal to or smaller than a second predetermined value.

* * * * *